United States Patent
Ooms et al.

(10) Patent No.: US 9,475,751 B2
(45) Date of Patent: *Oct. 25, 2016

(54) PROCESS FOR PRODUCING DIALKYL CARBONATES

(71) Applicant: Bayer MaterialScience AG, Leverkusen (DE)

(72) Inventors: Pieter Ooms, Krefeld (DE); Friedhelm Risse, Köln (DE); Andre Düx, Bornheim (DE); Carsten Buchaly, Düsseldorf (DE); Thomas Pancur, Altenholz (DE); Arthur Susanto, Köln (DE); Georg Ronge, Singapore (MY); Johan Vanden Eynde, Zwijnaarde (BE); Wim Wuytack, Zele (BE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/646,212

(22) PCT Filed: Nov. 19, 2013

(86) PCT No.: PCT/EP2013/074150
§ 371 (c)(1),
(2) Date: May 20, 2015

(87) PCT Pub. No.: WO2014/079835
PCT Pub. Date: May 30, 2014

(65) Prior Publication Data
US 2015/0299097 A1 Oct. 22, 2015

(30) Foreign Application Priority Data
Nov. 21, 2012 (EP) ..................... 12193568

(51) Int. Cl.
C07C 68/06 (2006.01)
C07C 29/128 (2006.01)

(52) U.S. Cl.
CPC ........... *C07C 68/065* (2013.01); *C07C 29/128* (2013.01); *C07C 29/1285* (2013.01)

(58) Field of Classification Search
None
See application file for complete search history.

(56) References Cited

U.S. PATENT DOCUMENTS

| 3,642,858 A | 2/1972 | Frevel et al. |
|---|---|---|
| 3,803,201 A | 4/1974 | Gilpin et al. |
| 4,062,884 A | 12/1977 | Romano et al. |
| 4,162,200 A | 7/1979 | Himmele et al. |
| 4,181,676 A | 1/1980 | Buysch et al. |
| 4,307,032 A | 12/1981 | Krimm et al. |
| 4,661,609 A | 4/1987 | Knifton |
| 4,691,041 A | 9/1987 | Duranleau et al. |
| 4,734,519 A | 3/1988 | Dunski et al. |
| 5,231,212 A | 7/1993 | Buysch et al. |
| 5,359,118 A | 10/1994 | Wagner et al. |
| 5,360,923 A | 11/1994 | Nickel et al. |
| 6,930,195 B2 | 8/2005 | Buchanan et al. |
| 7,763,745 B2 | 7/2010 | Van Der Heide et al. |
| 8,552,214 B2 | 10/2013 | Ooms et al. |
| 2011/0144371 A1 | 6/2011 | Ooms et al. |
| 2011/0237819 A1* | 9/2011 | Ooms ................... C07C 68/065 558/277 |

FOREIGN PATENT DOCUMENTS

| EP | 0001082 A1 | 3/1979 |
|---|---|---|
| EP | 0001083 A1 | 3/1979 |
| EP | 0180387 A2 | 5/1986 |
| EP | 0298167 A1 | 1/1989 |
| EP | 530615 A2 | 3/1993 |
| EP | 569 812 A1 | 11/1993 |
| EP | 581115 A2 | 2/1994 |
| EP | 592883 A1 | 4/1994 |
| EP | 889 025 A1 | 1/1999 |
| EP | 1086940 A1 | 3/2001 |
| EP | 1174 406 A1 | 1/2002 |
| EP | 2322261 A2 | 5/2011 |
| EP | 2354115 A2 | 8/2011 |
| JP | 2003104937 A | 4/2003 |
| WO | WO-2007/096340 A1 | 8/2007 |
| WO | WO-2007096343 A1 | 8/2007 |

OTHER PUBLICATIONS

International Search Report for PCT/EP2013/074150 mailed May 9, 2014.

* cited by examiner

*Primary Examiner* — Rebecca Anderson
*Assistant Examiner* — Po-Chih Chen
(74) *Attorney, Agent, or Firm* — Drinker Biddle & Reath LLP

(57) ABSTRACT

The present invention relates to a continuous process for producing lower dialkyl carbonates as a main product and alkylene glycol as a by-product by transesterification of a cyclic alkylene carbonate (e.g. ethylene or propylene carbonate) with lower alkyl alcohols in the presence of a catalyst and also the necessary purification of the dialkyl carbonate in a subsequent process step. For optimization of the economic efficiency and energy efficiency of the process, additional devices are used for intermediate heating of the internal liquid streams within the apparatus.

7 Claims, 1 Drawing Sheet

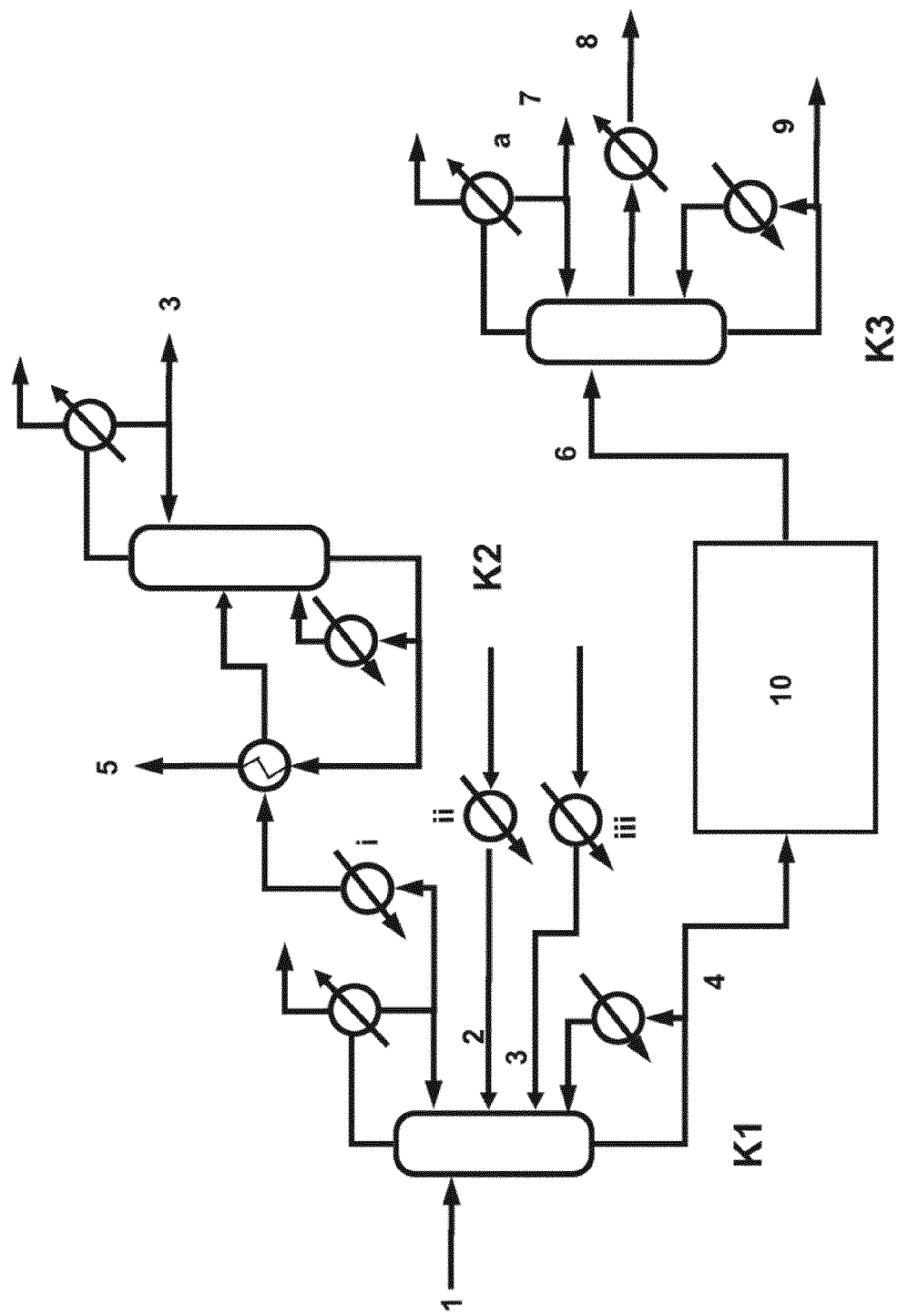

PROCESS FOR PRODUCING DIALKYL CARBONATES

CROSS-REFERENCE TO RELATED APPLICATIONS

This application is a national stage application (under 35 U.S.C. §371) of PCT/EP2013/074150, filed Nov. 19, 2013, which claims benefit of European Application No. 12193568.8, filed Nov. 21, 2012, both of which are incorporated herein by reference in their entirety.

The present invention relates to a continuous process for preparing lower dialkyl carbonates as main product and alkylene glycol as by-product by transesterifying a cyclic alkylene carbonate (e.g. ethylene carbonate or propylene carbonate) with lower alkyl alcohols in the presence of a catalyst, and the requisite purification of the dialkyl carbonate in a downstream process step. To optimize the economic viability and energy efficiency of the process, additional devices are used for intermediate heating of the internal liquid streams within the apparatus.

The preparation of dialkyl carbonates from cyclic alkylene carbonate and alkyl alcohol, in which alkylene glycol simultaneously forms as a by-product, is known and has been described many times. U.S. Pat. No. 6,930,195 B described this catalyzed transesterification reaction as a two-stage equilibrium reaction. In the first reaction stage, the cyclic alkylene carbonate reacts with alkyl alcohol to give hydroxyalkyl alkyl carbonate as an intermediate. The intermediate is then converted in the second reaction stage with the aid of alkyl alcohol to give the following products: dialkyl carbonate and alkylene glycol.

For the industrial implementation of the dialkyl carbonate preparation process, the use of a reactive distillation column (also referred to hereinafter as transesterification column), which has already been described in documents including EP 530 615 A, EP 569 812 A and EP 1 086 940 A, has been found to be particularly favorable. In EP 569 812 A, the cyclic alkylene carbonate is introduced continuously into the upper part of the transesterification column, and the dialkyl carbonate-containing alkyl alcohol into the middle or lower part of the transesterification column. In addition, below the introduction of the dialkyl carbonate-containing alkyl alcohol, virtually pure alkyl alcohol is introduced. The high boiler mixture, which includes the alkylene glycol prepared as a by-product, is drawn off continuously at the bottom of the transesterification column. The low boiler mixture, which comprises the dialkyl carbonate prepared, is drawn off at the top of the transesterification column as dialkyl carbonate/alkyl alcohol mixture and subjected to a further purification step.

The distillation column for the purification of the dialkyl carbonate/alkyl alcohol mixture is operated at a higher pressure than that in the transesterification column, such that a further dialkyl carbonate/alkyl alcohol mixture having a lower dialkyl carbonate content can be drawn off at the top of this distillation column. The dialkyl carbonate as main product is obtained at the bottom of this purification column with high purity.

There are many factors that are important for the development of an economically attractive preparation process for dialkyl carbonates. Most literature sources are concerned with the reaction parameters, for example conversion, selectivity or else product purity. A less common theme is the energy efficiency of the process (for example in EP 569 812 A, JP 2003-104937, WO 2007/096340, WO 2007/096343), even though these factors make a not inconsiderable contribution to the economic attractiveness of the process. Therefore, in this invention, measures are introduced in order to increase the energy efficiency of the process.

In EP 569 812 A, energy use in the preparation of the dialkyl carbonate is reduced by not condensing many internal process streams but conducting them as vaporous streams.

WO 2007/096340 describes a process in which alkylene carbonate is produced from alkylene oxide and $CO_2$ and then the alkylene carbonate is reacted with alkyl alcohol to give dialkyl carbonate and alkylene glycol, with purification of the mixture comprising dialkyl carbonate and alkylene glycol that arises in the second step. The reaction to give alkylene carbonate is exothermic, and the corresponding alkylene carbonate product stream is used to heat up the dialkyl carbonate/alkylene glycol product stream in the purification.

In WO 2007/096343, the mixture of dialkyl carbonate and alkyl alcohol that forms from alkylene carbonate and alkyl alcohol in a transesterification column is purified by means of extractive distillation, with alkylene carbonate serving as extractant. Once the dialkyl carbonate has been separated from the extractant by distillation, the hot bottoms output from this column, comprising the extractant, is used to heat the alkyl alcohol supplied to the transesterification column.

JP 2003-104937 considers various process variants for workup of an ethylene carbonate/ethylene glycol mixture and provision of the purified ethylene carbonate for the process for preparing dimethyl carbonate from the point of view of energy consumption among others.

However, none of the documents cited describes processes or procedures by which the reaction of alkylene carbonate with alkyl alcohol in the transesterification column can be performed in a particularly energy-efficient manner while maintaining the quality of the main product (dialkyl carbonate) and of the by-product (alkylene glycol). Therefore, in this invention, measures are introduced in order to increase the energy efficiency in this process step.

There was therefore a need for a process which firstly has a higher energy efficiency in the transesterification column and secondly only has an insignificant influence on the quality of the dialkyl carbonate and the alkylene glycol.

Because of the favorable influence on the temperature profile in the transesterification column and hence also on the reaction conversion, preference is given to the modes of operation in which both the virtually pure and the dialkyl carbonate-containing alkyl alcohol stream are fed in gaseous form to the transesterification column. These modes of operation also contribute to reducing the energy requirement for the reboiler in the transesterification column. For vaporization of the two streams, preference is given to using lower-grade steam or hot circulation water at a temperature level greater than $T_V$.

It has now been found that the energy efficiency can be increased by reducing the demand for external thermal energy, i.e. that generated outside the present process, which is required for operation of the heat exchanger(s) for vaporization of the alkyl alcohol streams, by, in a particularly simple and favorable manner, with the same product quality, recovering the condensation energy in the column for purification of the alkylene glycol and feeding it directly or indirectly to the heat exchangers for vaporization of the alkyl alcohol streams.

The thermal energy obtained in the top condenser of the alkylene glycol purification column or else the thermal energy obtained in other chemical preparation processes, at the temperature level $T_K$, can be fed either directly or indirectly to the heat exchanger(s) for vaporization of the alkyl alcohol streams. In the case of direct feeding, the stream which is to be condensed or cooled, by means of the heat exchanger(s), heats or vaporizes the alkyl alcohol stream(s) fed to the transesterification column. In the case of indirect feeding, the stream to be condensed or cooled, mediated by one or more heat transfer media, heats the alkyl alcohol-containing streams fed to the transesterification column. Useful heat transfer media include gases, vapors or liquids, preferably vaporous or liquid technical heat transfer media, for example water, heat carriers based on mineral oil or synthetic heat carriers (e.g. Diphyl™, Marlotherm®).

Particularly preferred heat transfer media are water or water vapor. In the downstream process stages for workup of the alkylene glycol prepared in the transesterification column, a large amount of waste heat arises, which has to be removed, for example, in the respective top condenser of the workup columns. This heat is typically not utilized, either because the temperature level is too low or the heat content is too low.

It has been found that, surprisingly, in the last workup stage for preparation of alkylene glycol, waste heat is obtained at a sufficient temperature level and a sufficient amount to be usable in another part of the process. More preferably, this waste heat is obtained from the top condenser from the alkylene glycol workup column. This waste heat can be used, for example, to preheat the feed in the dialkyl carbonate workup column or to vaporize the alcohol for the transesterification column. Particular preference is given to using the waste heat for vaporization of the virtually pure alkyl alcohol stream and/or the dialkyl carbonate-containing alkyl alcohol stream which are/is fed to the transesterification column.

The reduction in the consumption of external thermal energy with simultaneous retention of the high product quality results in a significant economic advantage through the process according to the invention.

The abovementioned thermal integration can be implemented, for example, by direct thermal connection in a common heat exchanger or by indirect thermal connection with the aid of a circulation fluid (e.g. water) as heat carrier. The utilization of the waste heat from the alkylene glycol workup column results in a significant economic advantage through the process according to the invention.

Dialkyl carbonates purified in the context of the invention are preferably those of the general formula (I)

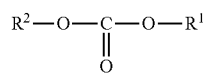
(I)

where $R^1$ and $R^2$ are each independently linear or branched, optionally substituted $C_1$-$C_{34}$-alkyl, preferably $C_1$-$C_6$-alkyl, more preferably $C_1$-$C_4$-alkyl. $R^1$ and $R^2$ may be the same or different. $R^1$ and $R^2$ are preferably the same.

$C_1$-$C_4$-Alkyl in the context of the invention is, for example, methyl, ethyl, n-propyl, isopropyl, n-butyl, sec-butyl, tert-butyl; $C_1$-$C_6$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2, 2-trimethylpropyl, 1-ethyl-1-methylpropyl, 1-ethyl-2-methylpropyl or 1-ethyl-2-methylpropyl; $C_1$-$C_{34}$-alkyl is additionally, for example, n-heptyl and n-octyl, pinacyl, adamantyl, the isomeric menthyls, n-nonyl, n-decyl, n-dodecyl, n-tridecyl, n-tetradecyl, n-hexadecyl or n-octadecyl. The same applies to the corresponding alkyl radical, for example in aralkyl or alkylaryl radicals. Alkylene radicals in the corresponding hydroxyalkyl or aralkyl or alkylaryl radicals are, for example, the alkylene radicals corresponding to the above alkyl radicals.

The above lists are illustrative and should not be understood as a limitation.

Preferred dialkyl carbonates are dimethyl carbonate, diethyl carbonate, di(n-propyl) carbonate, di(isopropyl) carbonate, di(n-butyl) carbonate, di(sec-butyl) carbonate, di(tert-butyl) carbonate or dihexyl carbonate. Particular preference is given to dimethyl carbonate or diethyl carbonate. Very particular preference is given to dimethyl carbonate.

The dialkyl carbonates are preferably prepared from cyclic alkylene carbonates having the formula (II):

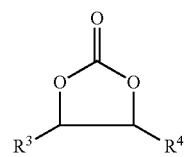
(II)

where, in the formula, $R^3$ and $R^4$ may each independently be hydrogen, substituted or unsubstituted $C_1$-$C_4$-alkyl, substituted or unsubstituted $C_2$-$C_4$-alkenyl or substituted or unsubstituted $C_6$-$C_{12}$-aryl, and $R^3$ and $R^4$ together with the two three-membered ring carbon atoms may be a saturated carbocyclic ring having 5-8 ring members. Preference is given to using ethylene carbonate or propylene carbonate as cyclic carbonate.

The cyclic alkylene carbonates are reacted with alkyl alcohols of the form

where $R^5$ is a straight-chain or branched $C_1$-$C_4$-alkyl. Preference is given to using methanol or ethanol as alkyl alcohol.

Transesterification catalysts used for production of the dialkyl carbonates are those known to those skilled in the art, for example hydrides, oxides, hydroxides, alkoxides, amides or salts of alkali metals, such as lithium, sodium, potassium, rubidium and caesium, preferably of lithium, sodium and potassium, more preferably of sodium and potassium (U.S. Pat. No. 3,642,858 A, U.S. Pat. No. 3,803,201 A, EP 1 082 A). In the case of use of the alkoxides, they can also be formed in situ, by using the elemental alkali metals and the alcohol to be converted. Salts of the alkali metals may be those of organic or inorganic acids, such as those of acetic acid, propionic acid, butyric acid, benzoic acid, stearic acid, carbonic acid (carbonates or hydrogencarbonates), of hydrochloric acid, hydrobromic acid or hydriodic acid, nitric acid, sulfuric acid, hydrofluoric acid, phosphoric acid, hydrogen cyanide, hydrogen thiocyanate, boric acid, stannic acid, $C_1$-$C_4$ stannoic acids or antimony acids. Preferred compounds of the alkali metals are the oxides, hydroxides, alkoxides, acetates, propionates, benzoates, carbonates and hydrogencarbonates; particular preference is given to using hydroxides, alkoxides, acetates, benzoates or carbonates. Such alkali metal compounds (optionally formed in situ from the free alkali metals) are used in amounts of 0.001% to 2% by weight, preferably 0.003% to 1.0% by weight, more preferably 0.005% to 1.0% by weight, based on the reaction mixture to be converted.

It is optionally possible to add complexing substances to such alkali metal compounds. Examples include crown ethers such as dibenzo-18-crown-6, polyethylene glycols or bicyclic nitrogen-containing cryptands.

Complexing agents of this kind are used in amounts of 0.1 to 200 mol %, preferably in 1 to 100 mol %, based on the alkali metal compound.

Suitable catalysts for the preparation of dialkyl carbonates are also thallium(I) and thallium(III) compounds, such as the oxides, hydroxides, carbonates, acetates, bromides, chlorides, fluorides, formates, nitrates, cyanates, stearates, naphthenates, benzoates, cyclohexylphosphonates, hexahydrobenzoates, cyclopentadienylthallium, thallium methoxide, thallium ethoxide, preferably Tl(I) oxide, Tl(I) hydroxide, Tl(I) carbonate, Tl(I) acetate, Tl(III) acetate, Tl(I) fluoride, Tl(I) formate, Tl(I) nitrate, Tl(I) naphthenate and Tl(I) methoxide (EP 1 083). The amounts of thallium catalyst are not particularly critical. They are generally 0.0001%-10% by weight, preferably 0.001%-1% by weight, based on the overall reaction mixture. In the preparation process, it is also possible to use nitrogen bases as catalysts (U.S. Pat. No. 4,062,884). Examples include sec- or tert-amines such as triethylamine, tributylamine, methyldibenzylamine, dimethylcyclohexylamine among others.

The amounts of the nitrogen bases used are from 0.01% to 10% by weight, preferably from 0.1% to 5% by weight, more preferably from 0.1 to 1% by weight, based on the overall reaction mixture. Usable catalysts are also compounds from the group of the phosphines, stibines, arsines or the divalent sulfur and selenium compounds, and the onium salts thereof (EP 180 387, U.S. Pat. No. 4,734,519).

Examples include the following: tributylphosphine, triphenylphosphine, diphenylphosphine, 1,3-bis(diphenylphosphino)propane, triphenylarsine, trimethylarsine, tributylarsine, 1,2-bis(diphenylarsino)ethane, triphenylantimony, diphenyl sulfide, diphenyl disulfide, diphenyl selenide, tetraphenylphosphonium halide (Cl, Br, I), tetraphenylarsonium halide (Cl, Br, I), triphenylsulfonium halide (Cl, Br) etc.

The preferred amounts used of this catalyst group are in the range from 0.1% to 10% by weight, preferably from 0.1% to 5% by weight, more preferably in the range from 0.1% to 2% by weight, based on the overall reaction mixture.

Further usable catalysts are compounds of tin, titanium or zirconium (U.S. Pat. No. 4,661,609 A). Examples of such systems are butylstannoic acid, tin methoxide, dimethyltin, dibutyltin oxide, dibutyltin dilaurate, tributyltin hydride, tributyltin chloride, tin(II) ethylhexanoate, zirconium alkoxides (methyl, ethyl, butyl), zirconium(IV) halides (F, Cl, Br, I), zirconium nitrate, zirconium acetylacetonate, titanium alkoxides (methyl, ethyl, isopropyl), titanium acetate, titanium acetylacetonate etc.

The amounts of these catalysts usable in accordance with preference are 0.1% to 10% by weight, preferably 0.1% to 5% by weight, based on the overall mixture.

In the preparation process, it is additionally possible to use bifunctional catalysts of the formula (III)

$$[A_aX_b]_m \cdot [B_cY_d]_n \quad (III).$$

In these bifunctional catalysts, the molar ratio of the two components in square brackets is expressed by the indices m and n. These indices may each independently assume values of 0.001-1, preferably 0.01-1, more preferably 0.05-1 and most preferably 0.1-1. Between the square brackets are neutral salts each composed of a cation and an anion. The indices a and b are each independently integers of 1-5; the indices c and d are each independently integers of 1-3, and the valence requirements of the cations and anions for formation of such neutral salts should be met. In addition, in (III), A is the cation of a metal which belongs to the third period and group IIa, the fourth period and group IIa, IVa-VIIIa, Ib or IIb, the fifth period and group IIa, IVa-VIIa or IVb, or the sixth period and group IIa-VIa of the Periodic Table of the Elements in the short period form.

The possible metals for the cation A are inferred by the person skilled in the art from the customary representations of the Periodic Table of the Elements (Mendeleev) in the short period form. A is preferably the cation of one of the metals Mg, Ca, Sr, Ba, Zn, Cu, Mn, Co, Ni, Fe, Cr, Mo, W, Ti, Zr, Sn, Hf, V and Ta, preferably the cation of one of the metals Mg, Ca, Zn, Co, Ni, Mn, Cu and Sn. Apart from the non-complexed cations of the metals mentioned, cationic oxo complexes of the metals mentioned are also an option, for example titanyl $TiO^{++}$ and chromyl $CrO_2^{++}$.

The anion X belonging to the cation A is that of an inorganic or organic acid. Such an inorganic or organic acid may be monobasic or dibasic or tribasic. Such acids and their anions are known to those skilled in the art. Examples of anions of monobasic inorganic or organic acids are: fluoride, bromide, chloride, iodide, nitrate, the anion of an alkanecarboxylic acid having 1-18 carbon atoms and benzoate; examples of anions of dibasic inorganic or organic acids are: sulfate, oxalate, succinate, fumarate, maleate, phthalate and so forth; examples of tribasic inorganic or organic anions are: phosphate or citrate. Preferred anions X in the catalyst of the formula (III) are: fluoride, chloride, bromide, iodide, sulfate, nitrate, phosphate, formate, acetate, propionate, oxalate, butyrate, citrate, succinate, fumarate, maleate, benzoate, phthalate, decanoate, stearate, palmitate, and laurate. Particularly preferred anions X are: chloride, bromide, iodide, acetate, laurate, stearate, palmitate, decanoate, nitrate and sulfate.

A useful cation B in the catalysts of the formula (III) is one from the group of the alkali metal or alkaline earth metal cations, the quaternary ammonium, phosphonium, arsonium or stibonium cations and the ternary sulfonium cations.

Alkali metal/alkaline earth metal cations in this context include: the lithium, sodium, potassium, rubidium, caesium, magnesium, calcium, strontium and barium cation, preferably the alkali metal cations mentioned, more preferably the sodium and the potassium cation.

Preferred cations B are those of the formula (IV)

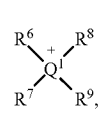

(IV)

in which $Q^1$ is N, P, As or Sb and $R^6$, $R^7$, $R^8$ and $R^9$ are each independently straight-chain or branched $C_1$-$C_{18}$ or $C_7$-$C_{12}$-aralkyl, and one of the $R^6$-$R^9$ radicals may also be $C_6$-$C_{12}$. B is more preferably a cation of the formula (V)

in which

Q² is N or P, preferably N.

Most preferably, in the context of the formulae (IV) and (V), the $R^6$, $R^7$, $R^8$ and $R^9$ radicals are replaced, respectively, by the $R^{16}$, $R^{17}$, $R^{18}$ and $R^{19}$ radicals, which are each independently straight-chain or branched $C_1$-$C_{18}$-alkyl or $C_7$-$C_8$-aralkyl and one of the $R^{16}$ to $R^{19}$ radicals may also be phenyl. Most preferably, in addition, the $R^{16}$, $R^{17}$, $R^{18}$ and $R^{19}$ radicals are replaced, respectively, by the $R^{26}$, $R^{27}$, $R^{28}$ and $R^{29}$ radicals, which are each independently $C_1$-$C_8$-alkyl or benzyl, and one of the $R^{26}$ to $R^{29}$ radicals may also be phenyl.

Straight-chain or branched $C_1$-$C_{18}$-alkyl is, for example, methyl, ethyl, propyl, isopropyl, butyl, isobutyl, hexyl, octyl, dodecyl, hexadecyl or octadecyl. Preferred alkyl has 1-12 carbon atoms; especially preferred alkyl has 1-8 carbon atoms.

$C_7$-$C_{12}$-Aralkyl is, for example, benzyl, phenylethyl, phenylpropyl, naphthylmethyl or naphthylethyl; preferred aralkyl is benzyl or phenylethyl; most preferred aralkyl is benzyl.

$C_6$-$C_{12}$-Aryl is, for example, phenyl, naphthyl or biphenylyl, preferably phenyl.

The anion Y in the catalyst of the formula (III) is a halide ion, such as fluoride, chloride, bromide or iodide, preferably bromide or iodide, more preferably iodide. However, it can also be defined as other anions mentioned under X if the anion X in the specific case is bromide or iodide.

The bifunctional catalyst of the formula (III) is used in an amount of 0.005%-5% by weight, preferably 0.01%-3% by weight, more preferably 0.01%-1% by weight, based on the overall transesterification mixture.

Such catalysts may be added to the top of the column in homogeneously dissolved form, in which case solvents employed are alkylene carbonate, alkylene glycol, alcohol or dialkyl carbonate, i.e. solvents endogenous to the system. It is of course possible to use insoluble transesterification catalysts disposed between the intermediate trays or among the random packings. In such a case, the metered addition of a dissolved catalyst via (2) may be dispensed with. Suitable heterogeneous catalysts are, for example:

ion exchange resins having functional groups formed from tertiary amines, quaternary ammonium groups, in which case examples of counterions include hydroxide, chloride or hydrogensulfate, sulfo groups or carboxyl groups, in which case examples of counterions for both include hydrogen, alkali metals or alkaline earth metals. These functional groups may be bound to the polymer either directly or via inert chains (U.S. Pat. No. 4,062,884 A, U.S. Pat. No. 4,691,041 A, EP 298 167 A). Mention should also be made of alkali metal or alkaline earth metal silicates, impregnated on silicon dioxide supports, and ammonium-exchanged zeolites.

The preparation process can be performed continuously or batchwise. Preference is given to a continuous mode of operation.

In the process, the cyclic alkylene carbonate compound(s) and the alkyl alcohol(s) are used preferably in a molar ratio of 1:0.1 to 1:40, more preferably of 1:1.0 to 1:30, most preferably of 1:2.0 to 1:20. The molar ratio specified does not take account of the recycling of cyclic alkylene carbonate compound or alkyl alcohol into the transesterification column via one or more top condenser(s) or one or more of any reboiler(s) present.

The catalyst is preferably introduced into the column via an introduction site above the introduction sites of the alkyl alcohol, together with the stream comprising the cyclic alkylene carbonate in dissolved or suspended form into the transesterification column. Alternatively, the catalyst can also be metered in separately, for example dissolved in the alkyl alcohol, in the alkylene glycol or in a suitable inert solvent. In the case of use of heterogeneous catalysts, they can be used in a mixture with the random packings mentioned, in a suitable shape in place of random packings or as a bed on any column trays installed.

The conversion of alkylene carbonate and alkyl alcohol to dialkyl carbonate and alkylene glycol takes place almost completely in a transesterification column. In preferred embodiments of the process for preparing dialkyl carbonate, the liquid stream withdrawn at the bottom of this transesterification column—optionally after concentration—can be subjected to a further reaction and/or purification in one or more further steps. Preferably, individual steps or all further steps of this kind can be effected in one or more further columns.

Useful transesterification columns or any second or further column(s) include columns known to those skilled in the art. These are, for example, distillation and rectification columns, preferably reactive distillation and reactive rectification columns.

A suitable column design for the distillation and/or reaction columns used in the process, which includes the design of the column height and of the column diameter, the selection of the column internals and the dimensioning of the feed and withdrawal lines, is known to those skilled in the art and can be taken from the relevant literature (for example Distillation Design, Henry Z. Kister, McGraw Hill; Distillation Operation, Henry Z. Kister, McGraw Hill; Perry's Chemical Engineering Handbook; Perry & Green).

With regard to the condensation in the top condenser, different embodiments are conceivable. Suitable top condensers are, for example, shell and tube or plate heat exchangers. The ratio $d_1/D_1$ of diameter of the vapor line from the column to the condenser ($d_1$) to the column diameter of the distillation column ($D_1$) is preferably in the range from 0.2 to 1.0, more preferably in the range from 0.5 to 1. In a particularly preferred embodiment, the top condenser may be integrated into the distillation column, such that no vapor line is required between distillation column and top condenser. The ratio $d_1/D_1$ in this case is 1. In this case, the column cross section after entry into the top condenser can also be adjusted to the progress of condensation under some circumstances.

In some condenser types, it may be advantageous to make the column cross section variable. When the vapors to be condensed are guided, for example, from the bottom upward, the amount of vapor decreases in the upward direction. A reduction in the column diameter in the direction of the top of the column allows the column cross section available for the vapor to be adjusted to the amount of vapor which decreases in the upward direction. In this case, the uncondensed vapors need not necessarily be withdrawn at the top. When, for example, a construction in which a plate bundle or tube bundle is inserted into the column from the top is selected, the withdrawal point of the uncondensed vapors may also be at the side.

The transesterification column preferably comprises at least one rectifying section in the upper part of the column and at least one reaction zone below the rectifying section. The rectifying section independently has 0 to 30 and preferably 0.1 to 30 theoretical plates.

In preferred embodiments, the transesterification column, below a reaction zone, has at least one stripping section having 0 to 20 and preferably 1 to 10 theoretical plates.

The transesterification column may further preferably be equipped with one or more reboiler(s). When the transesterification column is designed with a stripping section, preference is given to additionally using a reboiler which fully or partly evaporates the liquid effluxing from the stripping section. This fully or partially evaporated liquid stream is recycled fully or partly back into the transesterification column. In the case of an embodiment without a stripping section, in any reboiler used, the liquid effluxing from the reaction zone is evaporated fully or partly and recycled fully or partly back into the transesterification column.

The rectifying section(s) may, in preferred embodiments, be accommodated in the transesterification column together with the reaction section(s) and optionally at least one stripping section. In this case, the vaporous mixture coming from the reaction zone(s) is passed from below into a lower sector of the rectifying section and/or if appropriate into the lower rectifying section, which depletes the alkylene carbonate or alkylene glycol.

Below the reaction zone and any stripping section present, a mixture comprising alkylene glycol, excess or unconverted alkylene carbonate, alkyl alcohol, dialkyl carbonate, transesterification catalysts and high-boiling compounds which form in the reaction or are already present in the reactants is obtained. When a stripping section is used, the content of low-boiling compounds, for example dialkyl carbonate and alcohol, is reduced, forming further dialkyl carbonate and alkylene glycol under some circumstances in the presence of the transesterification catalyst. The energy required for this purpose is preferably supplied by one or more vaporizers.

In all sections of the transesterification column. i.e. both in the rectifying section and any stripping section, and in the reaction zone, random packings or structured packings can be used. The random packings or structured packings for use are those customary for distillations, as described, for example, in Ullmann's Encyclopädie der Technischen Chemie, 4th ed., vol. 2, p. 528 ff. Examples of random packings include Raschig or Pall and Novalox rings, Berl, Intalex or Torus saddles, Interpack bodies, and examples of structured packings include sheet metal and fabric packings (for example BX packings, Montz Pak, Mellapak, Melladur, Kerapak and CY packing) made of various materials, such as glass, stoneware, porcelain, stainless steel, plastic. Preference is given to random packings and structured packings which have a large surface area, good wetting and sufficient residence time of the liquid phase. These are, for example, Pall and Novalox rings, Berl saddles, BX packings, Montz Pak, Mellapak, Melladur, Kerapak and CY packings.

Alternatively suitable are also column trays, for example sieve trays, bubble-cap trays, valve trays, tunnel-cap trays. In the reaction zone(s) of the transesterification column, particular preference is given to column trays with high residence times coupled with good mass transfer, for example bubble-cap trays, valve trays or tunnel-cap trays with high overflow weirs. The number of theoretical plates of the reaction zone is preferably 3 to 50, more preferably 10 to 50 and most preferably 10 to 40. The liquid holdup is preferably 1 to 80%, more preferably 5 to 70% and most preferably 7 to 60% of the internal column volume of the reaction zone. The more exact design of the reaction zone(s), of any stripping section to be used and of the rectifying section(s) can be undertaken by the person skilled in the art.

The temperature of the reaction zone(s) is preferably in the range of 20 to 200° C., more preferably of 40 to 180° C., most preferably of 50 to 160° C. It is advantageous to perform the transesterification not only at atmospheric pressure, but also at elevated or reduced pressure. The pressure in the reaction zone is therefore preferably in the range of 0.2 to 20 bar, more preferably 0.3 to 10 bar, most preferably 0.4 to 5 bar. The pressure FIGURES given above and below—unless explicitly stated otherwise—are absolute pressure.

Preferably, the vapor mixture which comprises dialkyl carbonate and alkyl alcohol and is withdrawn at the top of the transesterification column in the process for preparing the dialkyl carbonate, after condensation at the top of the transesterification column, is supplied fully or partly to at least one further process step comprising at least one distillation column for separation of dialkyl carbonate and alkyl alcohol.

The dialkyl carbonate and the alkyl alcohol are preferably separated by distillation in one or more distillation columns or in a combination of distillation and membrane separation—referred to hereinafter as hybrid process (see, for example, U.S. Pat. No. 4,162,200 A. EP 581 115 B1, EP 592 883 B1 and WO 2007/096343A1).

When alkyl alcohol and dialkyl carbonate form an azeotrope (e.g. methanol and dimethyl carbonate), it is also possible to use a two-stage process, for example a two-pressure process, an extractive distillation, a heteroazeotrope distillation with a low-boiling azeotroping agent, or a hybrid process. Particular preference is given to employing the two-pressure process or a hybrid process.

Very particular preference is given to performing the separation of the dialkyl carbonate and the alkyl alcohol—even in the case that the dialkyl carbonate and the alkyl alcohol form an azeotrope—in a single distillation column. This distillation column is operated at a pressure higher than the pressure of the transesterification column(s). The operating pressure of the distillation column is in the range from 1 to 50 bar, preferably between 2 and 20 bar. At the bottom of the distillation column the virtually pure dialkyl carbonate is withdrawn, and at the top a mixture of dialkyl carbonate and alkyl alcohol. This mixture is supplied fully or partly to the transesterification column(s). When the process for preparing dialkyl carbonate is coupled with a process for preparing diaryl carbonate which is formed by transesterification of this dialkyl carbonate with an aromatic hydroxyl compound, a portion of the mixture of dialkyl carbonate and alkyl alcohol which is withdrawn at the top of the distillation column can be sent to an appropriate workup step for alkyl alcohol and dialkyl carbonate in the process stage for preparation of diaryl carbonate.

In a particularly preferred version, when the dialkyl carbonate and the alkyl alcohol form an azeotrope, this workup step is a two-pressure process. Such processes are known in principle to those skilled in the art (cf., for example, Ullmann's Encyclopedia of Industrial Chemistry, Vol. 7, 2007, Chap. 6.4. and 6.5.; Chemie Ingenieur Technik (67) 11/95).

When alkyl alcohol and dialkyl carbonate form an azeotrope, the distillate of a first distillation column of the process step for separating dialkyl carbonate and alkyl alcohol preferably has virtually azeotropic composition. In this case, it is preferably fed, in a two-pressure process, to at least one further distillation column which operates at an operating pressure below that of the first distillation column. As a result of the different operating pressure, the position of the azeotrope shifts toward lower proportions of alkyl alcohol. The bottom product obtained from this second distillation column or these further distillation column(s) is alkyl alcohol in a purity of 90 to 100% by weight, based on the total weight of the isolated bottom product, and the distillate obtained is a virtually azeotropic mixture. The second distillation column or further distillation column(s) which work at lower operating pressure is/are, in very particularly preferred embodiments, preferably operated with the heat of condensation of the top condenser(s) of the first distillation column.

The two-pressure process makes use of the pressure dependence of the azeotropic composition of a two-substance mixture. In the case of a mixture of alkyl alcohol and dialkyl carbonate, for example methanol and dimethyl carbonate, the azeotropic composition shifts to higher alkyl alcohol contents with increasing pressure. When a mixture of these two components is fed to a column (dialkyl carbonate column), the alkyl alcohol content being below the corresponding azeotropic composition for the operating pressure of this column, the distillate obtained is a mixture with virtually azeotropic composition and the bottom product virtually pure dialkyl carbonate. The azeotropic mixture thus obtained is fed to a further distillation column (alkyl alcohol column). This works at a lower operating pressure compared to the dialkyl carbonate column. As a result, the position of the azeotrope is shifted toward lower alkyl alcohol contents. This makes it possible to separate the azeotropic mixture obtained in the dialkyl carbonate column into a distillate with virtually azeotropic composition and virtually pure alkyl alcohol. The distillate of the alkyl alcohol column is fed back to the dialkyl carbonate column at a suitable point.

The operating pressure of the alkyl alcohol column is preferably selected such that it can be operated with the waste heat of the dialkyl carbonate column. The operating pressure is between 0.1 and 1 bar, preferably between 0.3 and 1 bar. The operating pressure of the dialkyl carbonate column is in the range of 1 to 50 bar, preferably between 2 and 20 bar.

A further preferred process for separating azeotropes of alkyl alcohol and dialkyl carbonate is the hybrid process. In the hybrid process, a two-substance mixture is separated by means of a combination of distillation and a membrane process. This makes use of the fact that the components, owing to their polar properties and their different molecular weight, can be at least partly separated from one another by means of membranes. In the case of a mixture of alkyl alcohol and dialkyl carbonate, for example methanol and dimethyl carbonate, when suitable membranes are used, by means of pervaporation or vapor permeation, an alkyl alcohol-rich mixture is obtained as the permeate and a mixture depleted in alkyl alcohol as the retentate. When a mixture of these two components is fed to a column (dialkyl carbonate column), the alkyl alcohol content being below the corresponding azeotropic composition for the operating pressure of this column, the distillate obtained is a mixture with a significantly increased alkyl alcohol content compared to the feed, and the bottom product virtually pure dialkyl carbonate.

In the case of a hybrid process composed of distillation and vapor permeation, the distillate is withdrawn from the column in vaporous form. The vaporous mixture thus obtained is fed to a vapor permeation, optionally after superheating. This vapor permeation is conducted in such a way that approximately the operating pressure of the column is established on the retentate side and a lower pressure on the permeate side. The operating pressure in the column is 1 to 50 bar, preferably between 1 and 20 and more preferably between 2 and 10 bar. The pressure on the permeate side is between 0.05 and 2 bar. This affords, on the permeate side, an alkyl alcohol-rich fraction with an alkyl alcohol content of at least 70% by weight, preferably at least 90% by weight, based on the total weight of the fraction. The retentate, which contains a reduced alkyl alcohol content compared to the distillate of the column, is optionally condensed and fed back to the distillation column.

In the case of a hybrid process composed of distillation and pervaporation, the distillate is withdrawn from the column in liquid form. The mixture thus obtained is, optionally after heating, fed to a pervaporation. This is conducted in such a way that an identical or elevated operating pressure compared to the column is established on the retentate side, and a lower pressure on the permeate side. The operating pressure in the column is 1 to 50 bar, preferably between 1 and 20 and more preferably between 2 and 10 bar. The pressure on the permeate side is between 0.05 and 2 bar. This affords, on the permeate side, an alkyl alcohol-rich vaporous fraction with an alkyl alcohol content of at least 70% by weight, preferably at least 90% by weight, based on the total weight of the fraction. The liquid retentate, which contains a reduced alkyl alcohol content compared to the distillate of the column, is fed back to the distillation column. The evaporation of the permeate requires heat, which may not be present to a sufficient degree in the feed stream to the pervaporation. A membrane separation by means of pervaporation may therefore optionally be heated with additional heat exchangers, which are integrated or optionally inserted between a plurality of pervaporation steps connected in series.

In the case of a hybrid process, dialkyl carbonate and alkyl alcohol are more preferably separated by means of a combination of distillation and vapor permeation.

The heat required to separate alkyl alcohol and dialkyl carbonate is supplied at a temperature between 100° C. and 300° C., preferably between 100° C. and 230° C. and more preferably between 120° C. and 200° C.

The distillation column(s) for workup of the dialkyl carbonate preferably possess(es) a rectifying section having preferably 5 to 40 theoretical plates for concentration of the alkyl alcohol and a stripping section having preferably 5 to 40 theoretical plates for concentration of the dialkyl carbonate.

For workup, the bottom product from the transesterification column is sent to further process steps. For this purpose, it is possible to take different routes, for example a) conduct further reactions in order to remove unwanted secondary components (e.g. EP 889 025) or b) convert them by a reaction to compounds which are easier to remove (e.g. EP 1174 406) or c) undertake separating operations, for example distillation, extraction, etc. (e.g. EP 569 812).

After these process steps, the prepurified bottom product from the transesterification column, now containing alkylene glycol in a concentration of greater than 95% by weight, preferably greater than 97% by weight and more preferably greater than 98% by weight, is sent to a distillation column which purifies this product stream still further. This distillation column is also referred to as alkylene glycol workup column in the examples.

Optionally, any homogeneous catalyst still present, before being fed into the distillation column, can be discharged, for example, by means of a falling-film evaporator (EP 569 812 A) or in the column itself together with the bottom product obtained therein.

The distillation column preferably comprises at least one rectifying section in the upper part of the column and at least one stripping section below the rectifying section. The column has 0 to 100 and preferably 0.1 to 100 theoretical plates. Optionally, the alkylene glycol can be withdrawn at the top or in a side draw from the column, preference being given to withdrawing it as a sidestream.

The column is operated at 1 to 2000 mbar, preferably at 10 to 1000 mbar.

The process for preparing dialkyl carbonate is preferably conducted continuously.

ANNOTATIONS FOR FIG. 1

K1 transesterification column
K2 distillation column for separation of the mixture comprising dialkyl carbonate and alkyl alcohol
K3 distillation column for purification of the alkylene glycol
1 reactant stream comprising alkylene carbonate and/or optionally catalyst
2 reactant stream comprising alkyl alcohol and dialkyl carbonate
3 reactant stream comprising virtually pure alkyl alcohol
4 stream comprising alkylene glycol
5 stream comprising purified dialkyl carbonate
6 stream comprising prepurified alkylene glycol
7 stream comprising low-boiling components inter alia
8 product stream comprising purified alkylene glycol
9 stream comprising high-boiling residues inter alia
10 process steps for prepurification of the alkylene glycol
a heat exchanger for recovery of the condensation energy
i, ii, iii heat exchangers in which the recovered condensation energy can be used to heat product streams

BRIEF DESCRIPTION OF THE DRAWINGS

FIG. 1 describes a transesterification step of alkylene carbonate and alkyl alcohol by means of reactive rectification in a first transesterification column (K1) in general, and the workup of the mixture comprising dialkyl carbonate and alkyl alcohol obtained at the top of the transesterification column in a distillation column (K2) and the final distillation of the alkylene glycol in a further distillation column (K3).

EXAMPLES

Using an example, the preferred mode of operation for the process according to the invention is indicated in detail. Examples 1 and 2 show the preferred method of waste heat utilization. This example should not in any way be interpreted as a limitation of the invention. The advantage of this invention, namely the reduction in the consumption of fresh heating steam, compared to other modes of operation, is shown in the comparative example.

Example 1

A reactive distillation column consisting of a rectifying section having 9 theoretical plates, a reaction zone having 25 reaction trays (holdup/tray: 0.6 m$^3$) and a stripping section having 4 theoretical plates is operated at a pressure of 400 mbar (absolute), measured at the top of the column, and a reflux ratio of 0.5.

Metered continuously into the upper column region directly above the first reaction tray are 9000 kg/h of ethylene carbonate and 175 kg/h of a mixture comprising 33.3% by weight of KOH and 66.7% by weight of ethylene glycol. Fed in between the 8th and 9th reaction trays are 16 854 kg/h of a vapor mixture comprising 83.7% by weight of methanol and 16.3% by weight of dimethyl carbonate. The methanol/dimethyl carbonate mixture is vaporized and superheated at 61° C. In addition, at the lower end of the reaction zone, 7078 kg/h of a vapor mixture comprising >99.9% by weight of methanol are fed in. The two methanol streams are vaporized and superheated at 62° C. For this purpose, 443 t/h of hot circulation water at 90° C. and only 1.1 t/h of heating steam at 1.5 bar (0.7 MW) are needed.

The top product obtained is 26 077 kg/h of distillate having a composition of 54.1% by weight of methanol and 45.6% by weight of dimethyl carbonate. The bottom product (7229 kg/h) includes 88.9% by weight of ethylene glycol, 6.7% by weight of methanol and 2.5% by weight of ethylene carbonate. Both the top product and the bottom product are sent to further purification steps.

The ethylene glycol workup column consists of 58 theoretical plates. The column is operated at a pressure of 50 mbar (absolute) measured at the top of the column and a reflux ratio of 36. 7026 kg/h of crude ethylene glycol having an ethylene glycol content of about 99% by weight are fed to the column between the 49th and 50th theoretical plates. In addition, 902 kg/h of crude ethylene glycol from the catalyst recovery column are returned between the 8th and 9th theoretical plates.

The top product obtained is 492 kg/h of distillate at 105° C. having a composition of 97.6% by weight of ethylene glycol and 0.4% by weight of ethylene carbonate, which can be used later as operating fluid for the vacuum system. The top condenser is used to produce 443 t/h of circulation water at 90° C. The bottom product (1200 kg/h) includes 94.3% by weight of ethylene glycol and 5.0% by weight of KOH, which is sent to further workup steps for recovery of the catalyst. 6230 kg/h of ethylene glycol (>99.9% by weight) is obtained as side product between the 28th and 29th theoretical plates.

Example 2

A reactive distillation column consisting of a rectifying section having 9 theoretical plates, a reaction zone having 25 reaction trays (holdup/tray: 0.6 m$^3$) and a stripping section having 4 theoretical plates is operated at a pressure of 400 mbar (absolute), measured at the top of the column, and a reflux ratio of 0.66.

Metered continuously into the upper column region directly above the first reaction tray are 9000 kg/h of ethylene carbonate and 175 kg/h of a mixture comprising 33.3% by weight of KOH and 66.7% by weight of ethylene glycol. Fed in between the 8th and 9th reaction trays are 21 371 kg/h of a vapor mixture comprising 83.7% by weight of methanol and 16.3% by weight of dimethyl carbonate. The methanol/dimethyl carbonate mixture is vaporized and superheated at 61° C. The heating medium used is 373 t/h of hot circulation water at 90° C. In addition, at the lower end of the reaction zone, 7123 kg/h of a vapor mixture comprising 99.5% by weight of methanol and 0.41% by weight of ethylene glycol are fed in. This almost pure methanol is vaporized and superheated at 74° C. For this purpose, 3.9 t/h of heating steam at 1.5 bar (2.4 MW) are required.

The top product obtained is 30 644 kg/h of distillate having a composition of 59% by weight of methanol and 41% by weight of dimethyl carbonate. The bottom product (7019 kg/h) includes 92.3% by weight of ethylene glycol, 6.7% by weight of methanol and 477 ppm of ethylene carbonate. Both the top product and the bottom product are sent to further purification steps.

The ethylene glycol workup column consists of 58 theoretical plates. The column is operated at a pressure of 50 mbar (absolute) measured at the top of the column and a reflux ratio of 36. 6876 kg/h of crude ethylene glycol having an ethylene glycol content of about 99% by weight are fed to the column between the 49th and 50th theoretical plates. In addition, 909 kg/h of crude ethylene glycol from the catalyst recovery column are returned between the 8th and 9th theoretical plates.

The top product obtained is 500 kg/h of distillate at 105° C. having a composition of 99.4% by weight of ethylene glycol and 0.4% by weight of ethylene carbonate, which can be used later as operating fluid for the vacuum system. The top condenser is used to produce 441 t/h of circulation water at 90° C. The bottom product (1200 kg/h) includes 94.8% by weight of ethylene glycol and 4.9% by weight of KOH, which is sent to further workup steps for recovery of the catalyst. 6203 kg/h of ethylene glycol (>99.9% by weight) is obtained as side product between the 28th and 29th theoretical plates.

Comparative Example 1

A reactive distillation column consisting of a rectifying section having 9 theoretical plates, a reaction zone having 25 reaction trays (holdup/tray: 0.6 m³) and a stripping section having 4 theoretical plates is operated at a pressure of 400 mbar (absolute), measured at the top of the column, and a reflux ratio of 0.66.

Metered continuously into the upper column region directly above the first reaction tray are 9000 kg/h of ethylene carbonate and 175 kg/h of a mixture comprising 33.3% by weight of KOH and 66.7% by weight of ethylene glycol. Fed in between the 8th and 9th reaction trays are 21 371 kg/h of a vapor mixture comprising 83.7% by weight of methanol and 16.3% by weight of dimethyl carbonate. In addition, at the lower end of the reaction zone, 7123 kg/h of a vapor mixture comprising 99.5% by weight of methanol and 0.41% by weight of ethylene glycol are fed in. The two methanol streams are vaporized and superheated at 61° C. and 74° C. respectively. For this purpose, 10.8 t/h of heating steam at 1.5 bar (6.8 MW) are required.

The top product obtained is 30 644 kg/h of distillate having a composition of 59% by weight of methanol and 41% by weight of dimethyl carbonate. The bottom product (7019 kg/h) includes 92.3% by weight of ethylene glycol, 6.7% by weight of methanol and 477 ppm of ethylene carbonate. Both the top product and the bottom product are sent to further purification steps.

The invention claimed is:

1. A process comprising preparing continuously both dialkyl carbonate of the formula $(R^1O)_2CO$, in which $R^1$ is a straight-chain or branched C1-C4-alkyl and alkylene glycol of the formula $HO-R^2-OH$, in which $R^2$ is a $C_2$-$C_4$-alkylene
by transesterifying cyclic alkylene carbonate with an alkyl alcohol of the formula $R^1OH$, in which $R^1$ is as defined above
in the presence of a catalyst in a transesterification column, by first purifying the alkylene glycol in a workup column producing a heat of condensation, wherein the heat of condensation of the alkylene glycol workup column is recovered and used directly or indirectly to vaporize at least one stream containing alkyl alcohol fed to the transesterification column.

2. The process for preparing dialkyl carbonate as claimed in claim 1, wherein the heat of condensation of the alkylene glycol workup column is used to preheat a feed in a dialkyl carbonate workup column or to vaporize the alkyl alcohol for the transesterification column.

3. The process as claimed in claim 1, wherein the transesterification column has a reaction zone having an upper, a middle and a lower section, and a stripping section beneath the reaction zone.

4. The process for preparing dialkyl carbonate as claimed in claim 3, wherein the transesterification is conducted in countercurrent in the presence of a catalyst in the transesterification column in such a way that alkylene carbonate stream is introduced into the upper section of the reaction zone of the column and a dialkyl carbonate-containing alkyl alcohol stream having a dialkyl carbonate content of 0.2% to 30% by weight into the middle or lower section of the reaction zone of the transesterification column.

5. The process for preparing dialkyl carbonate as claimed in claim 4, wherein the transesterification column is supplied with a further stream comprising alkyl alcohol, and wherein the further stream of alkyl alcohol is introduced beneath the dialkyl carbonate-containing alkyl alcohol stream.

6. The process for preparing dialkyl carbonate as claimed in claim 1, wherein the cyclic alkylene carbonate used is ethylene carbonate or propylene carbonate, and the alkyl alcohol used is methanol or ethanol.

7. The process for preparing dialkyl carbonate as claimed in claim 1, wherein the temperature in the reaction zone is in the range from 20 to 200° C. and the pressure is in the range from 0.2 to 20 bar.

* * * * *